Figure 1:
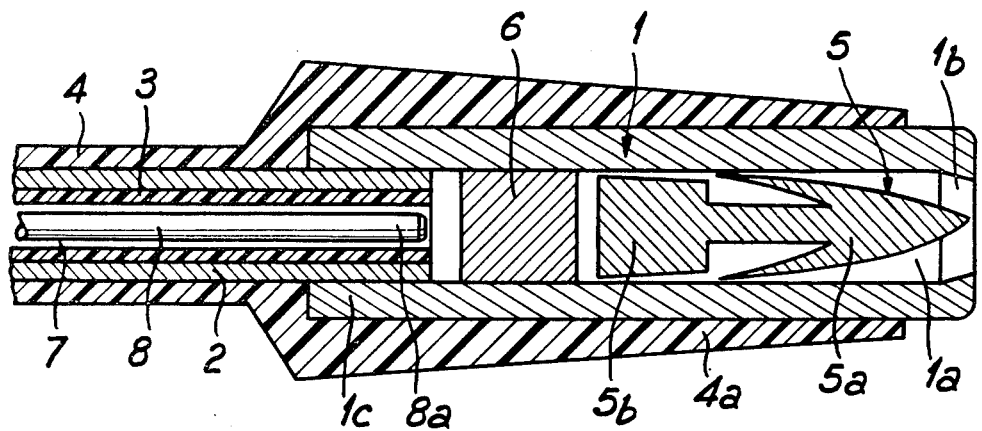

United States Patent [19]

Balat et al.

[11] 4,258,724
[45] Mar. 31, 1981

[54] ENDOCAVITARY CARDIAC STIMULATION PROBE

[75] Inventors: Roger Balat, Paris; Joseph A. Illes, Bourg-la-Reine; Jean-Francois V. Jacquemart, Paris; Christian Sarda, Serquigny, all of France

[73] Assignee: Synthelabo, Paris, France

[21] Appl. No.: 29,771

[22] Filed: Apr. 13, 1979

[30] Foreign Application Priority Data

Apr. 19, 1978 [FR] France .......................... 78 11512

[51] Int. Cl.³ .............................................. A61N 1/04
[52] U.S. Cl. ...................................... 128/785; 128/786
[58] Field of Search ........................... 128/784–786, 128/419 P, 642

[56] References Cited

U.S. PATENT DOCUMENTS

| 3,754,555 | 8/1973 | Schmitt | 128/785 |
| 3,976,082 | 8/1976 | Schmitt | 128/785 |
| 4,162,679 | 7/1979 | Reenstiema | 128/419 P |

FOREIGN PATENT DOCUMENTS

| 2133304 | 1/1973 | Fed. Rep. of Germany | 128/785 |
| 2453840 | 5/1976 | Fed. Rep. of Germany | 128/785 |
| 2187365 | 1/1974 | France | 128/785 |
| 2215978 | 8/1974 | France | 128/785 |
| 2302107 | 9/1976 | France | 128/785 |

Primary Examiner—Lee S. Cohen
Attorney, Agent, or Firm—Christel, Bean & Linihan

[57] ABSTRACT

The invention relates to an endocavitary cardiac stimulation probe. This probe comprises a tubular electrode connected to a cardiac stimulator by a flexible tubular insulated conductor. A harpoon, in solid biologically compatible material which can be resorbed during a period of the order of three weeks to three months, is mounted to slide in the tubular electrode in such manner that it can be extracted therefrom with a view to its being implanted in the endocavitary wall, by means of a thrust transmitted through the tubular conductor. This probe offers the advantage of being immobilized first by the harpoon and then, after resorption of the harpoon, by the natural formation of fibrose around the electrode.

13 Claims, 2 Drawing Figures

ENDOCAVITARY CARDIAC STIMULATION PROBE

The present invention relates to an endocavitary cardiac stimulation probe.

Probes of this kind are known that each comprise an electrode and a flexible externally insulated conductor for connecting said electrode to a cardiac stimulator. The end of a probe of this kind is introduced intravenously into a cardiac cavity so as to bring its terminal electrode into contact with the endocavitary zone to be stimulated. Only after a period which extends from three weeks to approximately three months does the formation of fibrose around the electrode guarantee attachment of the latter to the endocavitary zone to be stimulated. During the intermediate period there is a considerable risk, put at 4 to 15%, that the electrode of the probe will become displaced in relation to the precise zone to be stimulated, particularly under the effect of contractions of the myocardium.

For this reason, endocavitary cardiac stimulation probes have been designed that comprise means for attaching their electrodes in a permanent manner to the endocavitary zone to be stimulated. The electrodes of these improved probes comprise, at their end, anchoring members such as metallic barbs in various numbers, single or double helices made of metallic wire, etc. Certain of these anchoring members, particularly those consisting of metallic barbs, are not completely reliable since contractions of the myocardium may, in certain cases, cause them to become detached. Furthermore, removal of the probe, which is sometimes necessary, calls for detachment of its electrode and this involves the risk of causing local damage to the endocavitary wall. On the other hand, in the case where the electrode of a probe of this kind remains implanted in the endocavitary wall, considerable problems may be caused by incompatibility between the metallic anchoring element of said electrode and the cardiac wall. Finally, even after fibrose has formed around the electrode of such a sonde provided with an anchoring member, it has been found that said electrode has become displaced relative to the endocavitary zone to be stimulated; these phenomena which are extremely troublesome, are thought to be due to the mechanical actions to which the anchoring member or members is or are subjected as a result of contractions of the myocardium.

French Patent Applications Nos. 73.20916 and 75.06366, filed by Medtronic Inc. on 8th June, 1973 and 28th February, 1975 respectively, as well as German Patent Application 2 133 304, filed by I. Werner on 5th July 1971, all describe endocavitary cardiac stimulation probes, in which the members for anchoring the electrode that are formed by metallic barbs or hooks, suffer from the disadvantages mentioned above. Certain of these known probes comprise means for neutralizing the anchoring member when the electrode does not make contact with the endocavitary zone to be stimulated.

French Patent Application No. 74.03439, filed by Siemens A. G. on 1st February, 1974, describes an endocavitary cardiac stimulation probe, the electrode-immobilization member of which is formed by a small balloon, inflatable by a fluid supplied through a tube, to which is firmly connected a flexible conductor connecting the electrode to the cardiac stimulator. Such means for securing the electrode are not very reliable.

German Patent Application No. 2 453 840, filed by M. Lampadius on 13th November, 1974, describes an endocavitary cardiac stimulation probe having an electrode which may be bonded to the endocavitary zone to be stimulated, by means of an adhesive contained in a small reservoir fitted to the electrode. This adhesive may be an auto-polymerizing substance, compatible with the cardiac tissue and adapted to harden in combination with the liquid of said tissue and then to be resorbed by the cardiac tissue itself. Such a method of securing the stimulation electrode simply by bonding is likewise not very reliable.

A first object of the invention is to provide an endocavitary cardiac stimulation probe comprising an electrode, said electrode having a member for anchoring it to the endocavitary wall, and an externally insulated flexible conductor for connecting said electrode to a cardiac stimulator, this probe not suffering from the disadvantages, mentioned above, that affect the probes of this known kind.

A further object of the invention is to provide an endocavitary cardiac stimulation probe comprising an electrode provided with a member for anchoring it to the endocavitary wall, means for neutralizing the anchoring member while the electrode has not moved into contact with the endocavitary zone to be stimulated, and an externally insulated flexible conductor for connecting said electrode to a cardiac stimulator, said member for anchoring the electrode to the endocavitary wall being made, at least in its active portion, of a solid material which is biologically compatible and can be resorbed over a period of, in practice, between three weeks to three months.

It will be seen that the anchoring member of the probe that is neutralized during intravenous introduction of the probe becomes active only when the electrode of the probe has moved into contact with the endocavitary wall exactly in the zone to be stimulated. The anchoring member then penetrates into said endocavitary wall zone, to which it attaches said electrode in a perfectly reliable manner during the entire period, in the order of three weeks to three months, that is necessary for the natural formation of fibrose. Upon completion of this period, the anchoring member, or at least its active portion, is completely resorbed, but the electrode of the probe remains attached to the endocavitary zone to be stimulated by the fibrose that is formed. The electrode of the probe is thus prevented from becoming displaced relative to the endocavitary zone to be stimulated, during the initial period in the order of three weeks to three months, because of the presence of the anchoring member, and then, after the latter has been resorbed, because of the presence of the fibrose formed which ensures the final fixing of the electrode.

However, this final fixing of the electrode is not achieved by means of an anchoring member introduced permanently into the endocavitary wall. This results in the following advantages: since contractions of the myocardium do not apply direct mechanical action to the electrode of the probe, at least after absorption of its anchoring member, there no longer exists the risk of displacement of the electrode relative to the zone to be stimulated; furthermore, removal of the electrode no longer necessitates extraction of an anchoring member from the endocavitary wall so that the corresponding additional risks are eliminated.

In a preferred embodiment of the endocavitary cardiac stimulation probe in accordance with the invention, the electrode comprises a cavity, which has an opening at the end of the probe and in which cavity is lodged the anchoring member, and means are provided for extracting only the active portion of said anchoring member by way of the opening of said cavity when the electrode has moved into contact with the end cavitary zone to be stimulated. For example, the electrode may be of tubular shape, and the active portion of the anchoring member is carried by a part which is movable in said tubular electrode.

Extraction of the active portion of the anchoring member from the tubular electrode can be achieved by various means, to be described below:

In a first arrangement, the part carrying the active portion of the anchoring member, or a separate piston mounted to slide in the tubular electrode to the rear of the anchoring member, is made of a material which can be acted upon from a distance, for example a material sensitive to magnetic, electrical, or electromagnetic fields. Extraction of the active portion of the anchoring member and its implantation in the endocavitary wall can then be controlled by actions carried out at a distance therefrom, said actions being performed, in known manner, outside the body of the patient, in the area of the thorax.

In another arrangement, the flexible conductor, having an exterior insulating means, is in the form of a tube, for example of braided metal, for transmitting, from the extracardiac end of the probe, an extraction thrust to the anchoring member or to a piston mounted to slide in the tubular electrode to the rear of said anchoring member. The tubular electrode is rendered fluid-tight by means of suitable shaping of the part carrying the active portion of the anchoring member and/or of the piston. The agent for transmitting the extraction thrust may be a liquid, preferably a liquid silicone, with which the tubular conductor is filled. It may also be a flexible wire mounted to slide in the tubular conductor.

This latter form of construction is particularly advantageous in that it enables the electrode to be removed even during the initial period before fibrose forms and prior to the resorption of the anchoring member implanted in the endocavitary wall. For this purpose it in fact suffices to reintroduce, into the tubular conductor, the flexible wire which, during implantation, will have served to extract the anchoring member from the tubular electrode and for implanting it in the endocavitary wall, and then to apply to the anchoring member, directly or by way of the sliding piston and using this flexible wire or if necessary a more rigid wire, a thrust that is sufficient then to extract from the tubular electrode the part carrying the active portion of the anchoring member. When the anchoring member has moved completely from the tubular electrode, it is possible to retract the probe without risk of damaging the endocavitary wall, the anchoring member that remains therein being subsequently resorbed.

Figure 2:
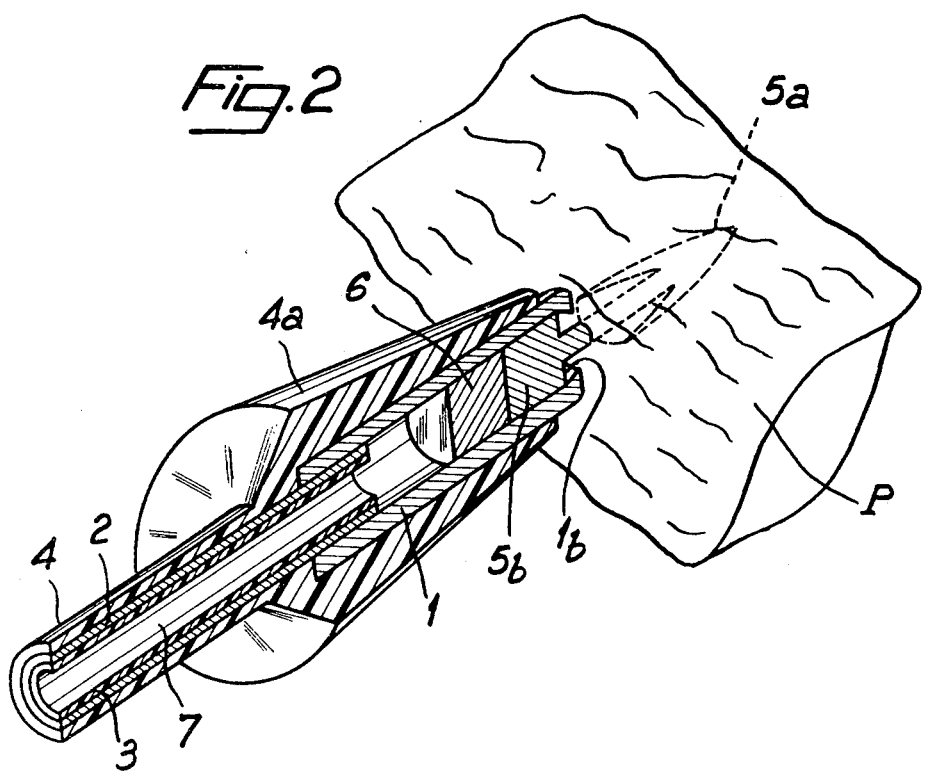

In order that the invention may be better understood, an embodiment thereof will now be described by way of example only and with reference to the accompanying drawings in which:

FIG. 1 is a view of that end of the probe that carries the tubular electrode, in a section along an axial plane of the electrode; and FIG. 2 is a part-sectional perspective view illustrating the implantation of the probe of FIG. 1 in an endocavitary wall.

Referring to FIG. 1, the reference numeral 1 designates a tubular electrode, made of platinum for example, the cylindrical bore 1a of which terminates, at the end of the probe, in an opening 1b which narrows slightly towards the exterior. Secured in the inner end 1c of the tubular electrode 1, by any suitable means, e.g. by welding, is the end of a flexible conductor 2 in the form of a tube of, for example, braided metal consisting of stainless steel wires. This tubular flexible conductor, only that portion of which that is near the electrode 1 being illustrated in FIG. 1, extends over the entire length of the probe, which length must be great enough to enable it to be introduced, through an artery, into the cardiac cavity in a known manner. The tubular conductor 2 is electrically insulated on its inside by a polyethylene sheath 3 which extends over its entire length. On the outside, the tubular conductor 2 is insulated by, for example, a layer 4 of silicone of medical quality which is moulded on to said tubular conductor 2; the silicone layer also extends along a zone 4a around the tubular electrode 1, but in such a manner as not to cover its outer end with the opening 1b formed therein.

Before use, the probe equipment as illustrated in FIG. 1 also comprises the following members: in the inner cylindrical cavity 1a of the tubular element 1 is fitted an anchoring member 5; this, in the embodiment shown, comprises an active portion 5a, which, for example, is in the form of a harpoon and is carried by a part 5b; the latter may be of frusto-conical shape for example, and its dimensions are such that its larger base, located towards the inner end of the tubular electrode 1, has a diameter slightly greater than the minimum diameter of the frusto-conical mouth portion 1b. The two portions 5a and 5b of the anchoring member 4 or of at least its active portion 5a are made of a solid material which is biologically compatible and can be resorbed over a period of the order of three weeks to three months. Such materials are well known and are used in particular for surgical sutures; use may be made in particular of catgut, that is to say twisted animal gut doped, for example with a material such as chromium so as to increase its resorption period; use may also be made of collagenous materials or synthetic materials that are biologically compatible and naturally resorbable over the periods indicated, for example a polymer of polyglycol acid or a copolymer of polyglycol acid (90%) and lactic acid (10%).

To the rear of part 5b of the anchoring member 5 and towards the inner end of the tubular electrode 1, a piston 6, made of platinum for example, is mounted to slide in the electrode. The circumferential surface of this piston 6 as well as the inner wall of the tubular electrode 1 have a suitable finish for ensuring that the probe is closed off in a liquid-tight manner from the interior of the tubular conductor 2 so as to prevent any penetration, into the inner channel 7, of biological liquids likely to rise to the end of said conductor which is connected to the cardiac stimulator (not illustrated); such rise of a more or less conductive biological liquid would result in the risk of short-circuiting the outlet of the cardiac stimulator and of preventing it from functioning correctly. Finally, a steel wire 8 is fitted to slide freely in the inner duct 7 of the tubular conductor 2, from which it is electrically insulated by the polyethylene sleeve 3; said wire 8 is preferably made of stainless steel.

To indicate the order of size of the head of the probe, illustrated on a large scale in FIG. 1, it should be stated that the tubular electrode 1, for example, preferably has an outside diameter in the order of 2.5 mm and an inside diameter in the order of 1.5 mm.

The head of the probe illustrated in FIG. 1 is introduced intravenously in the known manner into the cardiac cavity in which the zone to be stimulated is located. When the mount 1b of the tubular electrode 1 has moved into contact with the endocavitary wall P, as illustrated in FIG. 2, the operator pushes the extra-cardiac end of the metal wire 8 towards the interior, i.e. in the direction of the electrode 1, so that the end 8a of the wire 8 pushes the piston 6 towards the portion 5b of the anchoring member 5; displacement of a few millimeters of the wire 8 in the flexible but fixed sleeve 3-2-4, suffices to effect extraction, from the tubular electrode 1, of the active portion 5a of the anchoring member 5 by the action of the sealing piston 6. The active portion 5a of the anchoring member 5 then passes through the endocardium of the endocavitary wall P and then becomes completely inserted in the myocardium in the manner of a harpoon, whereas the portion 5b of the anchoring member 5 is retained in the end of the tubular electrode 1 because of the tapered form of the mouth 1b of said electrode. When the anchoring member 5 has been implanted, the operator pulls back the metal wire 8 of the probe, and the extra-cardiac end of the tubular conductor 2 of the probe can then be connected to the outlet of the cardiac stimulator in the known manner.

As indicated previously, the active portion 5a of the anchoring member 5 is completely resorbed when sufficient fibrose has developed around the free end of the tubular electrode 1 to cause the end of said electrode 1 to become permanently attached to the endocavitary wall P. Even prior to this complete resorption of the active portion 5a of the anchoring member 5, the probe can nevertheless be removed by introducing, into the inner duct 7, a metal wire such as that shown at 8, or a wire of slightly greater diameter and therefore of greater rigidity that permits, by way of the piston 6, a thrust to be applied to the portion 5b of the anchoring member 5, which thrust is sufficient to cause said portion 5b of the tubular electrode 1 to emerge completely through the tapered opening 1b of the electrode. The anchoring member 5 thus having been completely separated from the electrode 1, it then becomes possible to retract the entire probe.

The probe in accordance with the present invention can be provided in various forms that differ from that previously described but that all fall within the ambit of the invention: if the flexible wire 8 is made of an electrically insulating material or is covered with a sheath of such material, it becomes possible to dispense with the polyethylene sleeve 3 intended to provide interior insulation for the tubular conductor 2. The extraction thrust may be transmitted by way of the piston 6 to the anchoring member 5, not by a solid wire 8 but by a liquid, liquid silicone in particular, with which the inner duct 7 of the tubular conductor 2 is filled; in this case the extraction thust can be produced by means of a pump, in particular a piston pump, the delivery of which is connected to the extra-cardiac end of the inner duct 7 of the tubular conductor 2. The portion 5b of the anchoring member 5 that carries its active part 5a may also be so shaped as to ensure that the tubular electrode 1 is closed off in a liquid-tight manner from the interior of the tubular conductor 2; in this case, the piston 6 may be dispensed with. This portion 5b of the anchoring member 5 does not necessarily have to be made of a biologically compatible material or at least of a material that is resorbable, although this is preferable in case complete removal of the electrode is desired. In a particular arrangement, the part 5b of the anchoring member, or the piston 6 mounted to slide in the tubular electrode 1 to the rear of the anchoring member 5 may be made of a material sensitive to actions carried out at a distance, for example materials sensitive to magnetic, electrical or electro-magnetic fields; for instance, the part 5b of the anchoring member 5 and/or the piston 6 may be made, at least in part, of a magnetic material, sensitive to the action of an electromagnet, the displacement of which, outside the body of the patient and near his thorax, may then enable the anchoring member 5, or at least its active portion 5a, to be extracted from the tubular electrode 1. In this case the wire 8 can be dispensed with and possibly the piston 6 also, and the conductor 2 would not necessarily have to be of tubular form.

The tubular form of the electrode 1 and the cylindrical form of its cavity and consequently of the elements 5b and 6 located therein are likewise optional; the mode of operation, previously described by reference to FIG. 2, can be achieved with an electrode of any shape provided that it comprises a cavity which has an opening at the end of the probe, and in which is fitted the anchoring member.

The present invention also covers the replacement of the generally metallic anchoring members of previously known endocavitary cardiac stimulation probes by anchoring members made at least partly of a solid biologically compatible material which is resorbable over a suitable period.

We claim:

1. An endocavitary cardiac stimulation probe comprising an electrode, means carried by said probe and operatively associated with said electrode for anchoring said electrode to the endocavitary wall, means carried by said probe for neutralizing said anchoring means until said electrode is brought into contact with the endocavitary zone to be stimulated and it is desired to anchor said electrode to the endocavitary wall, and an externally insulated flexible conductor electrically connected to said electrode for connecting said electrode to a cardiac stimulator, said means for anchoring said electrode to the endocavitary wall being formed, at least in its active portion, of a solid biocompatible material which is resorbable over a period which in practice is between three weeks and three months.

2. A probe according to claim 1, wherein the electrode has a cavity which has an orifice, opening at one end of the electrode, and wherein is lodged the anchoring means, and wherein means are also provided for extracting only the active portion of said anchoring means through the orifice of said cavity when the electrode has moved into contact with the endocavitary zone to be stimulated.

3. A probe according to claim 2, wherein the electrode is of tubular form, and wherein the anchoring means has another portion carrying the active portion of the anchoring means that is movable in said tubular electrode.

4. A probe according to claim 3, wherein the portion carrying the active portion of the anchoring means and movable in the tubular electrode is made of a material that is sensitive to actions from a distance.

5. A probe according to claim 3, wherein a piston, made of a material sensitive to actions at a distance, is mounted to slide in the tubular electrode next to the anchoring means.

6. A probe according to claim 3, wherein the flexible externally insulated conductor is in the form of a tube suitable for the transmission of an extraction thrust from the extra-cardiac end of the probe to the anchoring means.

7. A probe according to claim 6, wherein the portion carrying the active portion of the anchoring means has a shape and size which sealingly co-operates with the tubular electrode to ensure that the cavity of the tubular electrode is fluid-tight.

8. A probe according to claim 6, wherein a piston respective to the extraction thrust is mounted to slide in the tubular electrode next to the anchoring means.

9. A probe according to claim 8, wherein the piston has a shape and size which sealingly co-operates with the tubular electrode to ensure that the cavity of the tubular electrode is fluid-tight.

10. A probe according to claim 6, wherein the medium for transmitting the extraction thrust is a liquid, particularly a liquid silicone, with which the tubular conductor is filled.

11. A probe according to claim 6, wherein the medium for transmitting the extraction thrust is a flexible wire mounted to slide in the tubular conductor.

12. A probe according to claim 6, wherein the medium for transmitting the extraction thrust is within the tubular conductor and is electrically conductive.

13. A probe according to claim 12, wherein the medium for transmitting the extraction thrust is a bare metal wire movable within the tubular conductor, and the tubular conductor is also insulated internally.

* * * * *

UNITED STATES PATENT AND TRADEMARK OFFICE
CERTIFICATE OF CORRECTION

PATENT NO. : 4,258,724
DATED : March 31, 1981
INVENTOR(S) : Roger Balat, Joseph A. Illes, Jean-Francois V. Jacquemart, Christian Sarda It is certified that error appears in the above-identified patent and that said Letters Patent are hereby corrected as shown below:

Claim 8, line 2, "respective" should be --responsive--.

Signed and Sealed this

Eighth Day of September 1981

[SEAL]

Attest:

GERALD J. MOSSINGHOFF

Attesting Officer

Commissioner of Patents and Trademarks